(12) United States Patent
Pickett et al.

(10) Patent No.: US 11,472,443 B2
(45) Date of Patent: Oct. 18, 2022

(54) MOBILE TRANSPORT SYSTEM AND METHOD FOR DELIVERING HEMS AND SERVICES

(71) Applicant: BIB Technologies, Inc., Los Angeles, CA (US)

(72) Inventors: Charles Deloss Pickett, Los Angeles, CA (US); Sean O'Keefe, Rock Springs, WY (US)

(73) Assignee: BIB Technologies, Inc., Los Angeles, CA (US)

(*) Notice: Subject to any disclaimer, the term of this patent is extended or adjusted under 35 U.S.C. 154(b) by 0 days.

(21) Appl. No.: 17/530,384

(22) Filed: Nov. 18, 2021

(65) Prior Publication Data

US 2022/0153312 A1 May 19, 2022

Related U.S. Application Data

(60) Provisional application No. 63/115,121, filed on Nov. 18, 2020.

(51) Int. Cl.
*B60W 60/00* (2020.01)
*B60P 3/00* (2006.01)
(Continued)

(52) U.S. Cl.
CPC ......... *B60W 60/00256* (2020.02); *A61L 2/10* (2013.01); *A61L 2/20* (2013.01); *A61L 2/24* (2013.01); *B60P 3/007* (2013.01); *B60P 3/20* (2013.01); *B60P 3/205* (2013.01); *A61L 2202/122* (2013.01); *A61L 2202/14* (2013.01); *A61L 2202/16* (2013.01); *B60W 2050/0004* (2013.01); *B60W 2710/242* (2013.01); *B60W 2710/305* (2013.01)

(58) Field of Classification Search
CPC ........ B60W 60/00256; A61L 2/10; A61L 2/20
See application file for complete search history.

(56) References Cited

U.S. PATENT DOCUMENTS 10,538,190 B1 * 1/2020 Metellus ................... B60F 5/02
11,275,942 B2 * 3/2022 Eyjolfsdottir ......... G06T 17/205
(Continued)

*Primary Examiner* — Jess Whittington
(74) *Attorney, Agent, or Firm* — Entralta; Peter D. Weinstein

(57) ABSTRACT

An apparatus and method for a mobile transport for delivering temperature-controlled contents includes a plurality of compartments each having an interior space and a front panel defining a wall. Each front panel opens in response to a predetermined condition. A temperature controller individually controls a temperature setting within at least one compartment, and a germicidal controller provides a germicide to the interior space of each compartment. In operation, the mobile transport receives an order signal including pickup location, customer identification, and delivery location. After the item has been placed in a compartment, the temperature controller sets the temperature setting for that compartment according to the item. The front panel of the compartment opens in response to receiving an open request signal satisfying the predetermined condition at the delivery location, the open request signal including information relating to the customer identification information.

22 Claims, 8 Drawing Sheets

(51) Int. Cl.
    *B60P 3/20*     (2006.01)
    *A61L 2/10*     (2006.01)
    *A61L 2/20*     (2006.01)
    *A61L 2/24*     (2006.01)
    *B60W 50/00*     (2006.01)

(56) References Cited

U.S. PATENT DOCUMENTS

| | | | |
|---|---|---|---|
| 2019/0034856 A1* | 1/2019 | High | G06Q 10/083 |
| 2019/0035044 A1* | 1/2019 | Ferguson | G05D 1/0295 |
| 2019/0043001 A1* | 2/2019 | Woulfe | G01C 21/3438 |
| 2019/0047356 A1* | 2/2019 | Ferguson | G06Q 50/28 |
| 2019/0176768 A1* | 6/2019 | Diaz Garcia | B60H 1/00357 |
| 2019/0180236 A1* | 6/2019 | Greenberger | G05D 1/0291 |
| 2019/0279181 A1* | 9/2019 | Kelly | G07F 9/023 |
| 2020/0090226 A1* | 3/2020 | Garden | G06V 20/56 |
| 2020/0130893 A1* | 4/2020 | Väin | G07C 9/30 |
| 2020/0262338 A1* | 8/2020 | Salter | B60Q 1/507 |
| 2021/0022536 A1* | 1/2021 | Anderson | G06Q 10/0832 |
| 2021/0346556 A1* | 11/2021 | Manka | A61L 2/24 |
| 2022/0051185 A1* | 2/2022 | Sato | H04L 63/08 |

\* cited by examiner

MOBILE TRANSPORT SYSTEM AND METHOD FOR DELIVERING HEMS AND SERVICES

PRIORITY

This application claims priority to provisional application 63/115,121 filed on Nov. 18, 2020. This application incorporates by reference provisional application 63/115,121 in its entirety.

BACKGROUND

Field

This disclosure relates to field of delivery systems and to an apparatus and method for securely and safely storing and delivering items and services.

Description of the Related Art

The Covid-19 pandemic has had a significant impact on a great number of markets and businesses. Among the markets impacted the most has been the food industry, particularly restaurants and other shops that provide food items to customers. From cooks to waiters to delivery people, the fear of transmission of the virus has had a devastating impact on the food industry. At the same time, the desire and demand for prepared food items has not waned, thus making it desirable to have a safer system and method for preparing and delivering food items to customers.

Although the food industry has been profoundly affected, the fear of transmission of the virus extends to other industries as well. Any market requiring interaction between providers and customers runs the risk of transmission. As a result, any items that can be provided and delivered to customers that minimizes or at least reduces human interactions correspondingly reduces the risk of transmission. A safer system for preparing and delivering non-food items, such as packages, furniture, clothing, medical products, pharmaceuticals, sundries, and other non-perishable items is therefore also desirable.

In addition to minimizing human interactions, the Covid-19 pandemic has also raised concerns about contact with materials or surfaces that may be supporting viruses, bacteria, or other germs. Science has shown that some bacteria and infectious diseases can last for days and perhaps longer on certain surfaces including paper, cardboard, plastic, packaging labels, Styrofoam, stamps, and tape. These concerns have made it desirable that delivery processes not only minimize human interactions, but also minimize contact with surfaces.

The delivery of items or services often requires the use of non-clean energy, like oil, gasoline, or kerosene to provide power for the device or transport providing the item or service. As climate change issues continue to have a negative impact on the environment, it would be desirable to use clean sources of energy to safely and securely deliver items and services.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1:
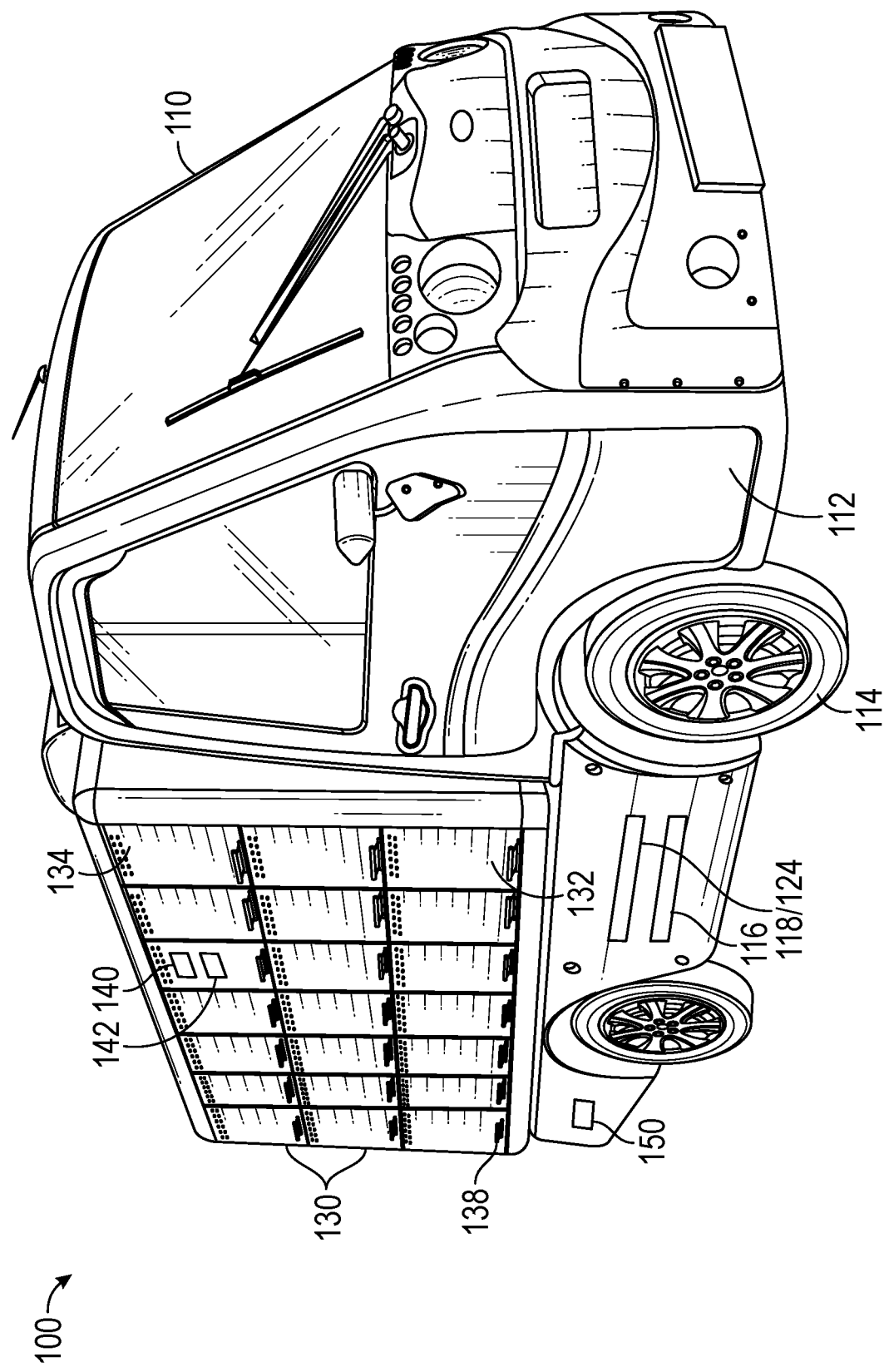
FIG. 1 shows an exemplary mobile transport according to an embodiment.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced using one or more implementations. In one or more instances, structures and components are shown in simplified form in order to avoid obscuring the concepts of the subject technology.

In the drawings referenced herein, like reference numerals designate identical or corresponding parts throughout the several views or embodiments.

FIG. 1 shows an exemplary mobile transport for safe and contactless delivery of items from a supplier to a customer according to an embodiment. As shown in FIG. 1, a mobile transport 100 includes a vehicle 110 having a body 112, wheels 114, a transmission 116, and a power source 118. Mobile transport also includes a plurality of compartments 130 coupled to the body 112 and an operational control unit 150.

The body 112 can be made of various materials, such as aluminum, steel, other metals, alloys, and/or fiberglass. The body 112 can include a cabin 120 with seating for one or more occupants and doors 122 to access the cabin. The body 112 can also include a bed 122 designed to couple to and support the compartments 130 and having a flat or other surface to facilitate the coupling to the compartments 130.

The transmission 116 is coupled to the body 112, the wheels 114, and the power source 118. The power source 118 can preferably include one or more batteries 124 that can be charged in a variety of ways including, for example, by plugging the batteries 124 to an external power source, through solar panels, or from other power sources as are known to those skilled in the art that are capable of charging a battery. The solar panels can be placed, for example, on the roof of the mobile transport 100 or on side panels of the mobile transport 100. The batteries 124 can be, for example, a lithium-ion battery or other battery types. The power source 118 can also be an internal combustion engine or a hybrid engine combining electrical power and gasoline power. Power output from the power source 118 is provided to the transmission 116 to power the transmission. The transmission 116 correspondingly converts the power received from the power source 118 into driving forces to cause the wheels 114 to move.

Alternatively, power source 118 can be provided by other alternative energy sources beyond solar including, for example, hydrogen or wind. These alternative energy sources can be combined with traditional energy sources and provide the ability to extend both range of the mobile transport 100 as well as provide for additional capacity for on-site operations such as thermal control, the generation of energy for storage, and third-party distribution of energy as a service. A micro wind turbine for power production can attached to the mobile transport 100 or pulled or accompanied with the mobile transport 100 by a trailer. Power from hydrogen can be implemented using micro-small-scale electrolyzer technology or hydrogen fuel cells. This capability of providing off-grid power production can be for the benefit of the operation of the mobile transport 100, as well as for power storage and the resale or distribution of the power stored from these alternative power sources, and thus acting like a mobile power station for other electric or hybrid vehicles or other devices that can be charged from the alternative power sources. It also allows the mobile transport 100 to have a zero-carbon footprint by providing alternative schemes for charging its own batteries required for motive power and operation of the mobile transport 100 without depending on energy from the grid, which may have been generated from fossil fuels, coal, or other non-clean energy.

The compartments 130, which are coupled to the body 112, each define an interior space 132 that can be used to store a variety of different items including, for example, foodstuffs, packages, mail, or any other items capable of fitting within the interior space 132. Each compartment 130 can have the same shape and size or can be of different sizes and shapes to accommodate items having different sizes and shapes. Each compartment 130 also includes a front panel 134. The front panel 134 is movable between an open and a closed position so that an item can be placed in and/or removed from the interior space 132.

In addition to serving as a door to access the interior space 132 of compartment 130, the front panel 134 can include a screen. The screen can be, for example, an LCD, plasma, or other type of display screen capable of displaying text, graphics, images, videos, and/or other data. The screen for the front panel 134 can provide a variety of information including advertisements for the company providing the item within the associated compartment 130, information regarding the contents of the compartment 130, or information to identify the customer to which the contents of the compartment is intended (such as a transaction ID or a customer ID that avoids identifying the customer or recipient by name). Instead of individual imaging or videos on each screen, the screens across all compartments 130 can be controlled and configured to form a unified image or video. The compartments 130 can also include lighting, such as lighting around the perimeter of each front panel 134. The lighting around a specific compartment can be activated, for example, when that compartment is going be used to accept an item or going to be accessed to remove an item, effectively serving as a visual indication to users or customers of the location to insert or remove an item. The front panel 134 can also be configured to be opaque to ensure that the content of the compartment 130 cannot be seen.

Each compartment 130 can also include other electronic components including, for example, one or more cameras, a keyboard, biometric reader, microphone, speaker, RFID, and/or LED lights or other form of indicators. These other electronic components can assist in controlling access to each compartment 130 and the opening and closing of the front panel 134, as will be explained in more detail herein.

The opening of the front panel 134 can be controlled by a lock 138 that moves the front panel 134 between an open position and closed, locked position. The lock 138 can include a motorized mechanism having, for example, a gas or hydraulic rod, a spring, a solenoid, and/or a servo unit. The lock 138 preferably includes electronic circuitry, such as a microprocessor, microcontroller, CPU, memory, RAM, and or ROM, configured to control the opening and closing of the front panel 134 in response to a received signal, as will be explained in more detail herein. The lock 138 are preferably tamper-proof and can only be activated to open a compartment 130 with the proper authorization, which provides significant security for the contents of items in the compartments 130.

In addition to the lock 138, each compartment 130 can includes a temperature controller 140 (though only one shown in FIG. 1). The temperature controller 140 preferably includes both heating and cooling elements that can control the temperature within the compartment 130 to be set to a particular or desired temperature setting. The temperature setting can be adjusted depending on the type of item provided within the compartment 130. For example, for food items that have just been prepared, the temperature controller 140 can be configured to be set to a higher than ambient temperature to keep the food items warm. Alternatively, if the food items are fresh produce or meats, then the temperature controller 140 can be configured to be set to a lower than ambient temperature to keep the food items cool. The temperature controller 140 can also include circuitry, such as a microprocessor, microcontroller, CPU, memory, RAM, and or ROM, that can be configured to receive control signals and, in response to those control signals, control the heating and/or cooling elements to set the temperature within the interior space 132 to a setting in accordance with the received control signals.

Each compartment 130 preferably also includes a germicidal controller 142 (though only one shown in FIG. 1) to reduce and/or eliminate the risk of germs being present in the compartment 130. The germicidal controller 142 can include, for example, an ultraviolet (UV) light that acts to provide germicidal irradiation of all surfaces and contents of the compartment 130. UV germicidal irradiation (UVGI) is an example of a disinfection method that uses short wavelength ultraviolet (UV-C) light to kill or inactivate microorganisms by destroying nucleic acids and disrupting their DNA, leaving them unable to perform vital cellular functions. To minimize risks associated with the use of UV-C light, the germicidal controller can preferably use "Far UVCI Light" emitters that are known to be safer for and not harmful to the environment. Such emitters include, for example, UVCI LED's. In addition, to ensure the UVGI is able to irradiate all surfaces, the germicidal controller 142 can include multiple sources of UVGI positioned at multiple locations within each compartment 130. The germicidal controller 142 can also use other forms of germicide instead of or in addition to UVGI. For example, the germicidal controller 142 can include a germicidal spray or gas that has a germicidal function such as ones including alcohol, hydrogen peroxide, chlorine, formaldehyde, glutaraldehyde, and/or phenol.

The germicidal controller 142 can also include circuitry, such as a microprocessor, microcontroller, CPU, memory, RAM, and/or ROM, that can be configured to receive control signals and, in response to those control signals, control the UVGI, spraying of the germicide, or other form of germicide to sanitize the compartment 130 in accordance with the received control signals. Through activation of the germicidal controller 142, it is possible to sanitize compartments 130 including the respective interior spaces 132 in which items are stored. Doing so creates a safe transfer of the items and further assists in the safety of the supply chain and logistics protocols by mitigating or eliminating exposure to disease-causing germs during the last step in delivery to a customer or end users.

The operation control unit 150 includes circuitry, such as a microprocessor, microcontroller, CPU, memory, RAM, and/or ROM, that can be configured to control all of the operations of the mobile transport 100 including, for example, movement from location to location, opening and closing of compartments 130, controlling the operation of the temperature controller 140, controlling the operation of the germicidal controller 142, controlling the operation of lighting, controlling access and storage of data received from businesses, users, and customers, and/or controlling the display of information, images, and/or videos on the display screens of the front panels 132. In addition to this operational functionality, operation control unit 150 preferably includes transmitters and receivers that can transmit and receive data and signals over a variety of transmission paths including cellular, Wi-Fi, Bluetooth, NFC via IoT or any other form of wired or wireless transmission. Operation control unit 150 can also include one or more cameras, a keyboard, biometric reader, microphone, speaker, RFID, and/or GPS circuitry. For storing and accessing data received from businesses, users, and customers, the operation control unit 150 can be configured to store the data in local memory, a hard drive, optical drive, distributed memory, or cloud storage.

Figure 2:
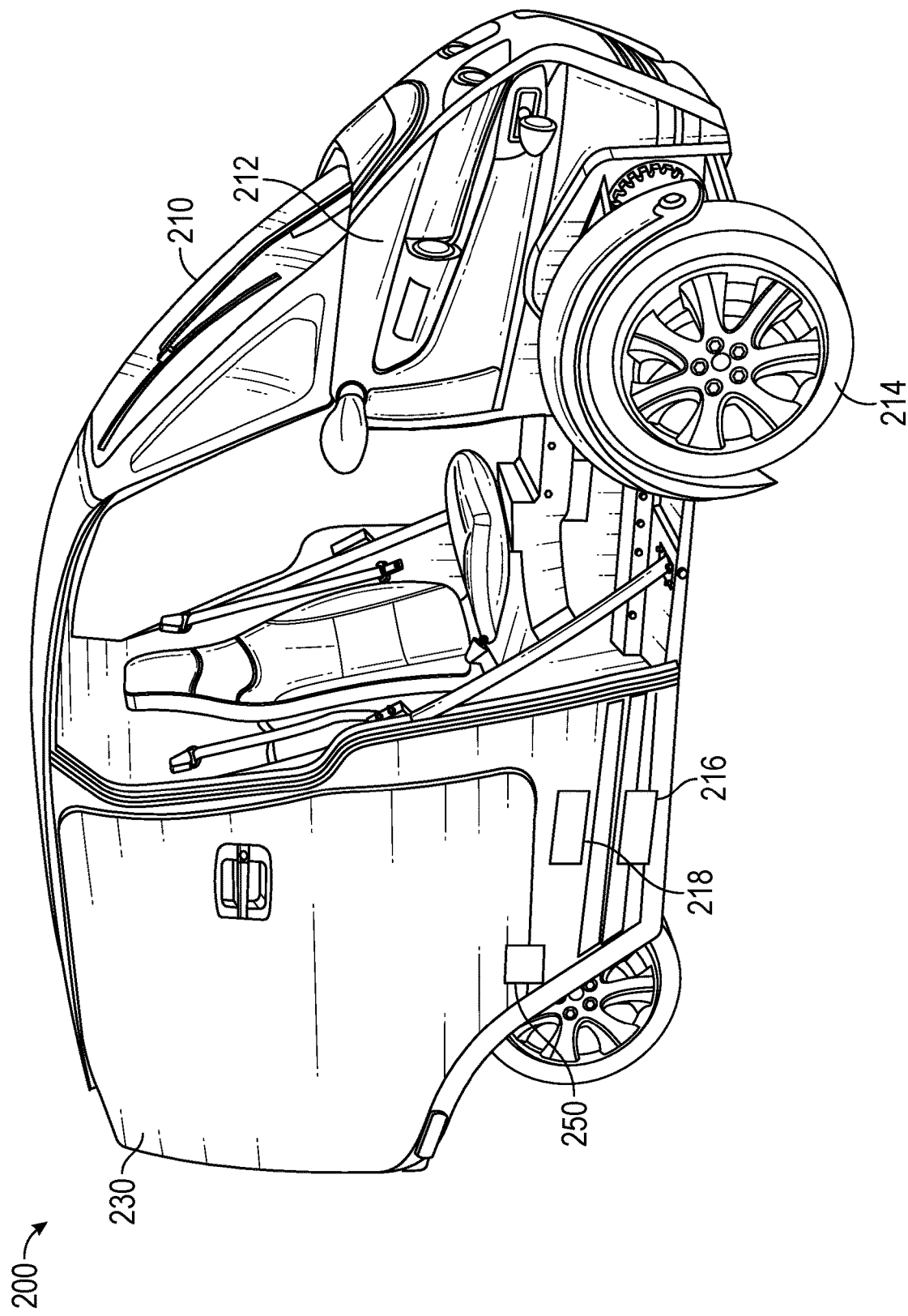
FIG. 2 shows an exemplary mobile transport according to another embodiment.

FIG. 2 shows an exemplary mobile transport for safe and contactless delivery of items from a supplier to a customer according to another embodiment. As shown in FIG. 2, a mobile transport 200 includes a vehicle 210 having a body 212, wheels 214, a transmission 216, and a power source 218. Mobile transport also includes a plurality of compartments 230 coupled to the body 212 and an operational control unit 250.

Mobile transport 200 can have the same structure and operation as the corresponding components of mobile transport 100, but with difference regarding sizes and numbers. For example, mobile transport 200 can be smaller, use fewer wheels, and have fewer compartments. The smaller size and corresponding lower weight can enable mobile transport 200 to have a longer range for delivery than mobile transport 100, operate at higher speeds on the road, and be recharged at a faster rate.

In addition to mobile wheeled vehicles, like mobile transports 100 and 200, the mobile transport can also be alternative conveyances that do not rely on wheels. For example, the mobile transport can also be a drone or other type of unaccompanied air vehicle or a boat. The mobile transport need only be sufficiently sized to include one or more compartments 130 and include the controllers and operation control unit of mobile transport.

Figure 3A:
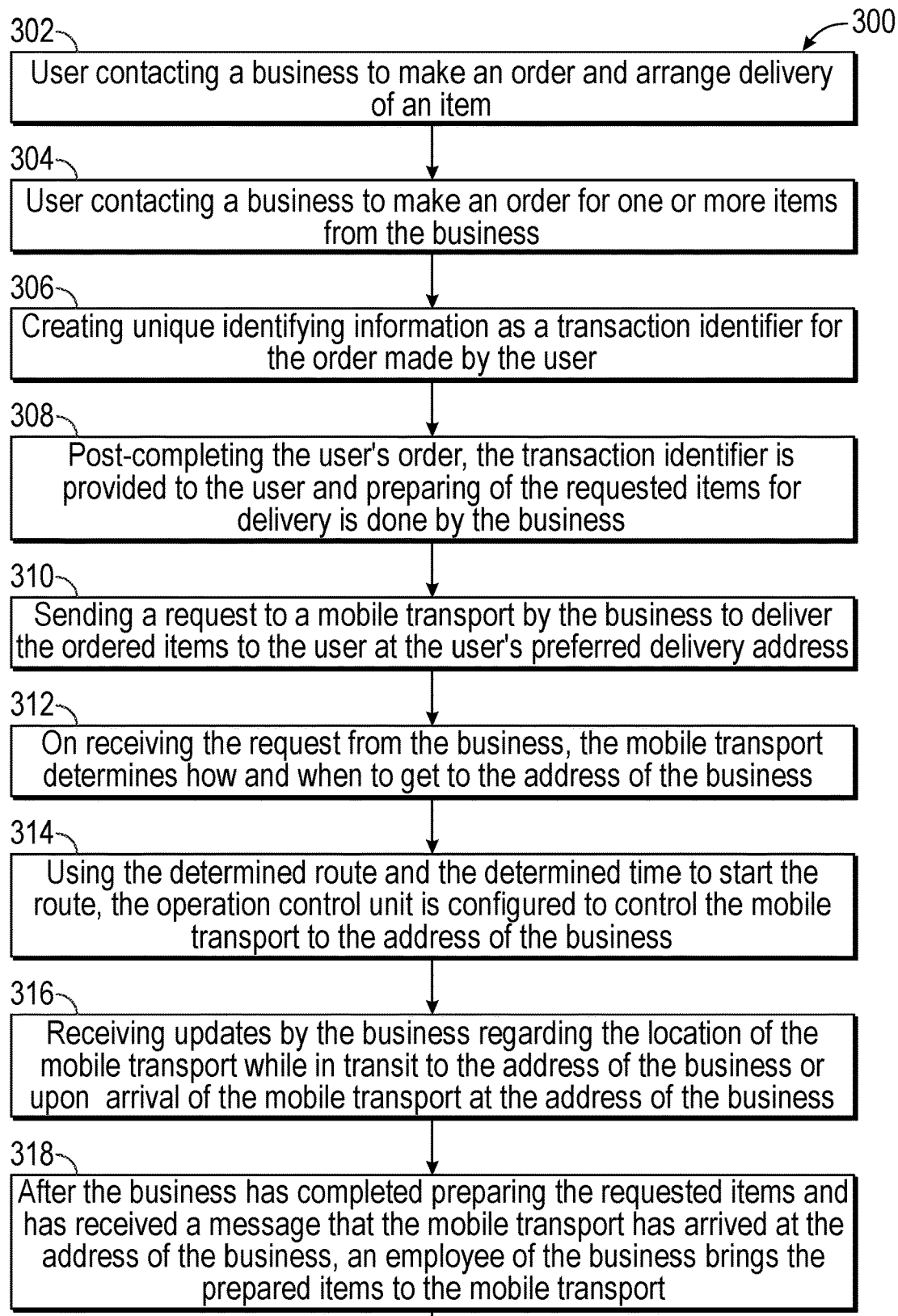
FIGS. 3A, 3B, and 3C (collectively FIG. 3) are a flow chart of an order and delivery process using a mobile transport according to an embodiment.
Figure 3B:
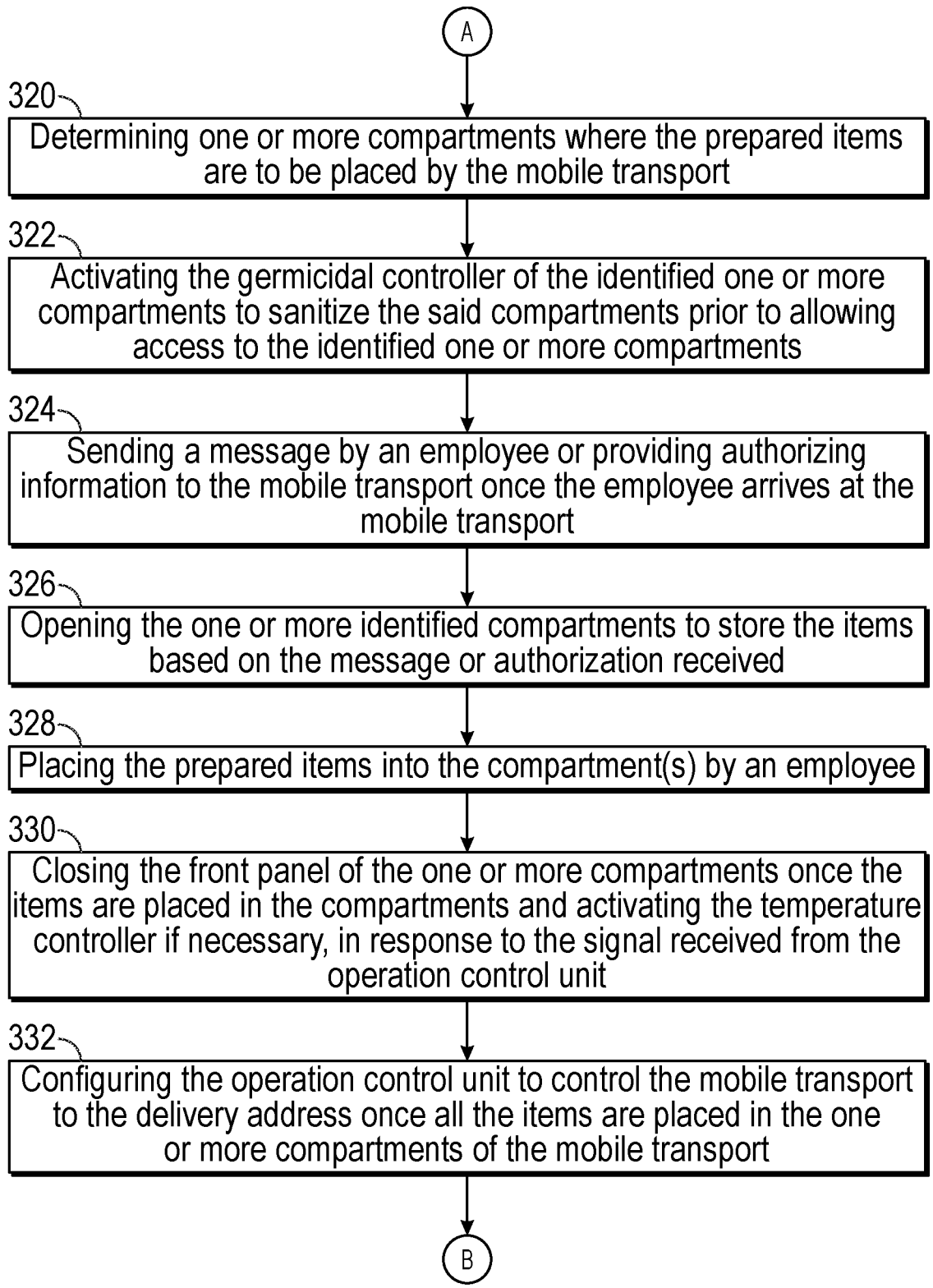
Figure 3C:
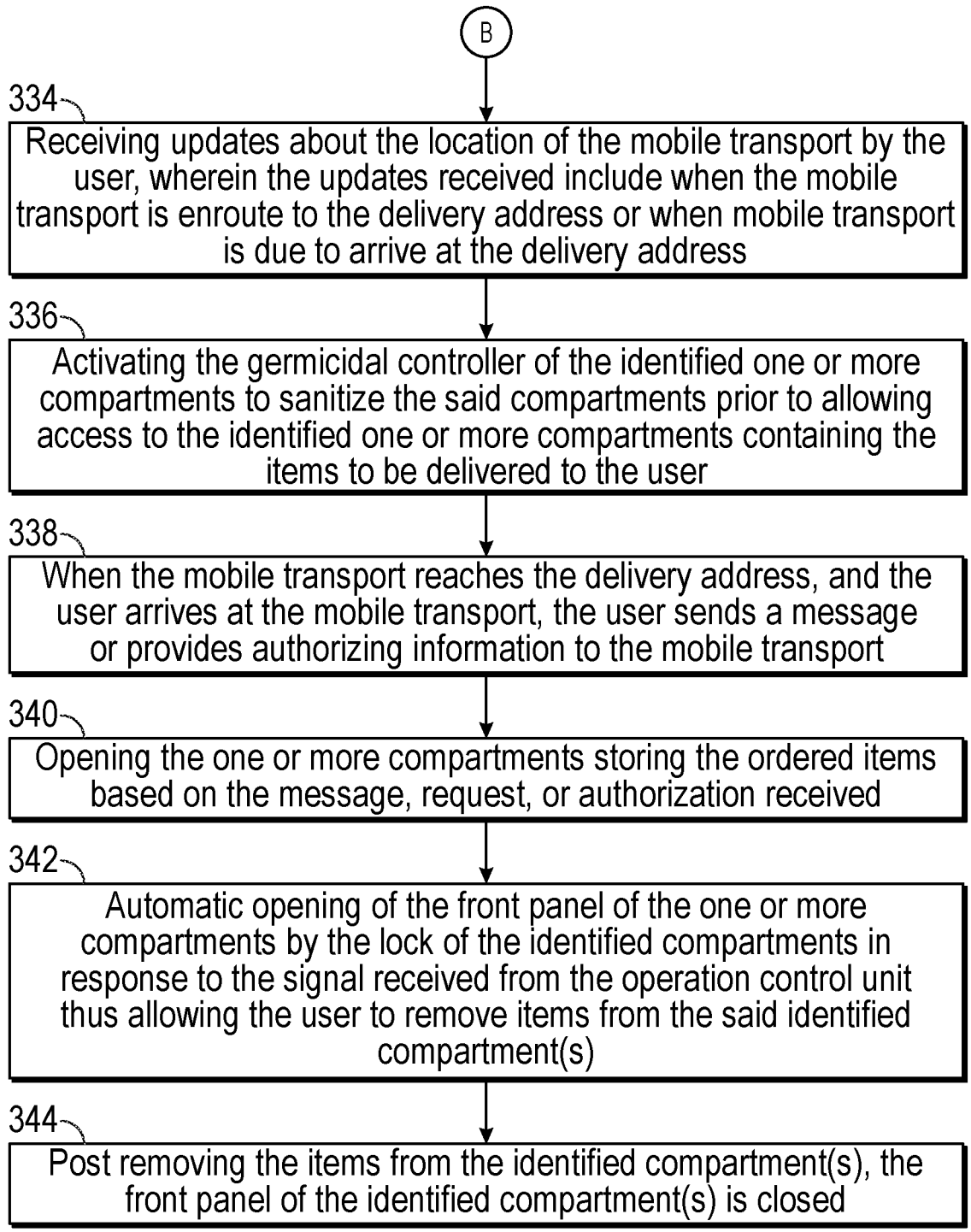

FIG. 3 is a flow chart of an order and delivery process using a mobile transport according to an embodiment. The order and delivery process of FIG. 3 is available for any business that provides items that can be stored and delivered in a mobile transport according to any of the disclosed embodiments and modifications thereof. As shown in FIG. 3, a user, such as a customer or other end user, contacts a business to make an order and arrange delivery of an item (step 302). The user can contact the business through for example, a website using a mobile device, cell phone, desktop computer, a laptop, tablet, or other computing device, or through an application running on such a device. Alternatively, the user may contact the business by phone or email. If it is a returning or existing user, the business may automatically recognize the user through cookies on the user's device and/or through a login or registration process completed by the user. The information associated with the user through that recognition can include the user's name, address, contact number, payment information, past orders, and preferences. These preferences can include identifying information about the user including, for example, biometric information like a facial ID or fingerprint, a code created by the user, or other data that uniquely identifies the user. These preferences can also include information about how the user prefers to have items delivered, a preferred delivery address, and a preferred identifier to use for accessing a compartment holding a user's ordered items (e.g., using facial ID or a transaction ID).

The user contacting the business can make an order for one or more items from the business (step 304). The items can be, for example, hot food, cold food, packages, mail, or any other type of consumer item that may fit within a compartment of a mobile transport. The order may be submitted through the business's website, application, or orally through a phone call. The order preferably includes information identify the requested items, the location to which to deliver the items, customer information, and any other information as may be needed to complete the order and make the delivery.

In response to the order, unique identifying information is created as a transaction identifier for the order by the user (step 306). The unique identifying information created for the transaction identifier can be, for example, a random number, a value created based on identification information of the user, a QR code, or any other unique value that can be used to uniquely identify the transaction corresponding to the order made by the user.

The transaction identifier is provided to the user (step 308). If the order was made through the business's website or application, the transaction identifier can be provided directly to the user's computing device through the corresponding website or application, sent by text, or sent by email. If the order has been made by phone, then an operator at the business can provide the user with the transaction identifier by phone.

Once the order has been completed and the transaction identifier has been provided to the user, the business prepares the requested items for delivery (step 308). This preparation may include, for example, cooking requested food items, collecting items from storage, and placing the requested items into some form of packaging. In addition, the business sends a request to a mobile transport (e.g., mobile transport 100 or 200) to be used to deliver the ordered items to the user at the user's preferred delivery address (step 310). The request can include the address of the business, the address to which to deliver the item, the transaction identifier, and/or preference information about the user including, for example, biometric information, a unique user code, or other unique user identifier. Since the preference information includes valuable private information about the user, any request sent to the mobile transport can be encrypted to minimize the risk of the preference information being compromised. The request can also include information about a desired pick-up time that, for example, minimizes the time between the completion of the preparation of the requested item and the placement of the requested item into the mobile transport. The request can be transmitted from the business to the mobile transport using any of a variety of communication methods including wirelessly via a cellular network or over a shared Wi-Fi network.

Alternatively, the business may possess one or more mobile transports, through purchase or leasing for example, and have the mobile transport available at its location whenever one or more deliveries need to be made. It also possible that the business uses the mobile transport to be used with items prepared at its discretion without any customer orders, fills the compartments 130 with those items, and has the mobile transport go to a location where customers can access and purchase the items stored in the compartments 130, thereby operating analogously to a food truck or portable vending machine.

In response to the request received from the business, the mobile transport determines how and when to get to the address of the business (step 312). The request can be received by a receiver in the operation control unit of the mobile transport. The operation control unit analyzes the content of the received request and extracts the address of the business from the received request. This analysis and extraction can be performed by circuitry in the operation control unit such as a microprocessor or CPU. The operation control unit also determines the current location of the mobile transport by using its GPS circuitry. Based on the current location of the mobile transport and the extracted address of the business, the operation control unit determines a route for the mobile transport to take from its current location to the address of the business. The determined route can also include an estimated time to complete the route based on the length of the route, the speed limits on the route, and the existing traffic along the route. The operation control unit also analyzes the content of the received request and extracts the desired pick-up time. Based on the current time, the desired pick-up time, and the determined route to the address of the business, the operation control unit can determine a time to begin the route to the address of the business to arrive at an optimal time that minimizes the time between the completion of the preparation of the requested items and the arrival of the mobile transport.

Using the determined route and the determined time to start the route, the operation control unit can be configured to control the mobile transport to the address of the business (step 314). If the mobile transport can be operated autonomously without human interaction, then the operation control unit can be configured to control the transmission and the steering of the mobile transport according to the determined travel route. For such autonomous operation, the operation control unit can use information from cameras to detect the outside environment and road conditions and use artificial intelligence as is known in the art to control the operation of the steering and transmission to ensure the mobile transport travels the route safely. Alternatively, the mobile transport can be driven by a human operator. In that case, the operation control unit can include a display to show the operator the route to the address of the business and provide oral instructions to the operator regarding where to turn along the route.

While in route to the address of the business, the business can receive updates about the location of the mobile transport including when it arrives at the address of the business (step 316). For example, the operation control unit can send messages to the business that include information about the current location of the mobile transport, as well as an estimated arrival time. The messages can be sent from a transmitter of the operation control unit using any of a variety of communication methods including, for example, wireless communication such as through a cellular or Wi-Fi network. The messages can be received by the business at any of a variety of computing devices including PC's, laptops, and mobile devices such as mobile phones or tablets.

When the business has completed preparing the requested items and has received a message that the mobile transport has arrived at the address of the business, an employee of the business brings the prepared items to the mobile transport (step 318). Based on the type of items to be delivered, the mobile transport determines one or more compartments in which the items are to be placed (step 320). For example, if the items need to be temperature controlled, the operation control unit can identify a compartment having the necessary temperature controller that controls the temperature of the compartment to be at a setting appropriate for the item. The operation control unit can also evaluate the size of the items and identify an appropriately sized compartment that can hold the items.

Before allowing access to the identified one or more compartments, the operation control unit can activate the germicidal controller of the identified compartment to sanitize the compartment (step 322). Activating the germicidal controller at this time provides multiple benefits. For example, by doing so prior to opening the compartment and allowing the employee to put the items in the compartment, the compartment will already have been sanitized before the employee is exposed to it. In addition, by limiting the activation of the germicidal controller to the compartments that are about to be used for a delivery, the mobile transport can conserve more energy and conserve resources, such as when using germicidal sprays.

When the employee arrives at the mobile transport, the employee can send a message or provide authorizing information to the mobile transport (step 324). The message sent by the employee can include information about the delivery including, for example, the transaction identifier or other unique identifier that enables the operation control unit of the mobile transport to determine whether to open a compartment and which one to open. The message can be sent from a computing device, such as a mobile phone or tablet, and received by a receiver of the operation control unit. Alternatively, instead of sending a message from a computing device, the employee can enter a code on a keypad located on the mobile transport or have biometric information examined such as by a facial scan, a retinal scan, or a fingerprint scan to ensure that the employee is authorized to place items into the identified compartment.

In addition, if the business has its own mobile transport, it can interface with the mobile transport to load one or more items of its choosing into one or more compartments of the mobile transport. In this case, instead of providing a message about the delivery, the message can include information about the item being placed into a compartment, the pricing of the item, any temperature control issues relating to the item, and any other relevant information regarding the item, its transport, and its sale.

Based on the received message or authorization, the one or more compartments for storing the items are opened (step 326). Using, for example, the transaction identifier included in the message or corresponding to the authorized employee, the operation control unit sends a signal to the lock of the identified compartment to open the front panel of the compartment. In response to the signal, the lock automatically opens the front panel of the compartment. At that point, the employee places the items into the compartment (step 328).

Once placed into the compartment, the front panel of the compartment is closed (manually or automatically), and the temperature controller is activated, if necessary (step 330).

The signal for the lock to close the front panel of the compartment can be provided by the operation control unit to the lock of the applicable compartment. The operation control unit sending the signal to the lock can be in response to a message or authorization from the employee, based on the elapsing of a specific time period, or based on a detection system that determines the items have been placed inside the compartment. The detection system can include, for example, motion detectors.

In addition, based on the type of items placed in the compartment, the operation control unit can signal the temperature controller for that compartment to control the temperature inside the interior space of the compartment to be set to an appropriate setting. For example, the temperature controller can receive a signal to set the interior temperature to keep the items warm or to keep the items cold. On the other hand, for non-perishable items and items having no need for maintaining a temperature warmer or cooler than the ambient temperature, the operation control unit need not send any signal to the temperature controller. It is also possible that when the need for a temperature controller is known in advance, the operation control unit can send a control signal to the temperature controller to start warming or cooling for a period of time before items are placed in the compartment.

Once all of the items have been placed in one or more compartments of the mobile transport, the operation control unit can be configured to control the mobile transport to the delivery address (step 332). The operation control can determine the route in the same manner as explained with respect to controlling the mobile transport to the address of the business. Similarly, while in route to the delivery address, the user can receive updates about the location of the mobile transport including when it arrives at the delivery address (step 334). For example, the operation control unit can send messages to the user that include information about the current location of the mobile transport, as well as an estimated arrival time. The messages can be sent from a transmitter of the operation control unit to any of a variety of computing devices of the user including PC's, laptops, and mobile devices such as mobile phones or tablets. The messages can be text messages, emails, or voice messages.

Before allowing access to the one or more compartments containing the items to be delivered to the user, the operation control unit can activate the germicidal controller of the identified compartments to sanitize them (step 336). Activating the germicidal controller at this time provides similar benefits including ensuring that the compartment will already have been sanitized before the user is exposed to it. Additionally, by limiting the activation of the germicidal controller to the compartments that are about to be opened for the user, the mobile transport can conserve more energy and conserve resources.

When the mobile transport reaches the delivery address, and the user arrives at the mobile transport, the user can send a message or provide authorizing information to the mobile transport (step 338). The message sent by the employee can include information about the delivery including, for example, the transaction identifier or other unique identifier that enables the operation control unit of the mobile transport to determine whether to open a compartment and which one to open. The message can be sent from a computing device, such as a mobile phone or tablet, and received by a receiver of the operation control unit. Alternatively, instead of sending a message from a computing device, the user can enter a code on a keypad located on the mobile transport, have a QR code scanned, or have biometric information examined such as by a facial scan, a retinal scan, or a fingerprint scan to ensure that the user is authorized to access the compartment holding the ordered items.

In the alternative, where the mobile transport includes items selected by the business and not in response to an order from a user, the user can send a request to purchase an item from within one of the compartments. To make the request to purchase, the user can similarly use a computing device, such as a mobile phone or tablet, a keypad, a QR code reader, or biometric reader, and the request can be received by a receiver of the operation control unit. For example, the user can access a website or app on the computing device that includes information about the contents of the compartments, identify a desired item, and purchase that item. Alternatively, the user can use a camera on a computing device that scans a QR code on the mobile transport, which directs the computing device to a web site through which the user identifies and purchases an item.

Based on the received message, request, or authorization, the one or more compartments storing the ordered items are opened (step 340). Using, for example, the transaction identifier included in the message or corresponding to the authorized user, the operation control unit sends a signal to the lock of the identified compartment to open the front panel of the compartment. In response to the signal, the lock automatically opens the front panel of the compartment. At that point, the user removes the items from the compartment (step 342). Once removed the compartment, the front panel of the compartment is closed (step 344). The signal for the lock to close the front panel of the compartment can be provided by the operation control unit to the lock of the applicable compartment. The operation control unit sending the signal to the lock can be in response to a message or authorization from the user, based on the elapsing of a specific time period, or based on a detection system that determines the items have been removed from the compartment.

The order and delivery process of FIG. 3 provides multiple benefits that make the order and delivery convenient, safe, and cost-effective for businesses and users ordering items. These benefits include, for example, the ability to apply germicides to compartments that are used to store and deliver items with the use of germicidal controllers before the compartments are accessed by business employees or users receiving deliveries. This ability minimizes or eliminates the risk of transmission of viruses and bacteria for both the business employees and the users receiving deliveries. The order and delivery process also automates the pick-up and delivery of items that can eliminate the need for dedicated delivery employees and/or dedicated delivery vehicles while also minimizing contacts between people.

The mobile transport can be configured to operate autonomously, thus obviating the need for dedicated delivery employees, and can be shared by multiple businesses, thus obviating the need for dedicated delivery vehicles. And with only one person placing the items in the compartments and only one person later removing the items, people-to-people contacts are avoided. By providing temperature controllers, the mobile transports can store and deliver items, particularly foodstuffs, while maintaining an appropriate temperature for those items, both above and below the ambient temperature.

The inclusion of screens on the front panels of the compartments also provides multiple benefits. These benefits include, for example, being able to promote and advertise businesses, both on a single screen and using multiple screens to provide unified images or videos promoting the same. The screens can also be used to provide information to employees about where to put items and to users about where to pick-up the items such as be providing messages or images giving indications about which items belong in which compartments.

The operation of the mobile transports and the process as described in FIG. 3 can be limited by geofencing. Geofencing is a location-based service in which an app or other software uses GPS, RFID, Wi-Fi, or cellular data to trigger a pre-programmed action when a mobile device or RFID tag enters or exits a virtual boundary set up around a geographical location, known as a geofence. With geofencing, the operation of the mobile transports can be limited to a set geographical area. As a result, mobile transports can be assigned to an exclusive geographical area such that other mobile transports are unable to operated in that area. Similarly, the mobile transport would be unable to operated outside of its assigned geofence.

Businesses and operators of the mobile transports can also use processes to keep track of items placed and sold in the mobile transports. For example, each item can include a tracking indicator, such as a bar code, RFID, NFC, or other unique identifier to track which items have been input to the mobile transport and have been sold and/or removed from the mobile transport. Through use of the tracking identifiers, the businesses can ensure proper authorized secure conveyance of the items by tracking the item throughout the delivery process. This tracking provides both an inventory monitoring measure as well as a security measure including against theft at any point in the transport and delivery process.

As previously mentioned, the mobile transport according to this application can provide the function of mobile energy source that both generates the energy and delivers the energy to customers, particularly for alternative energy sources like solar, wind, and hydrogen. For hydrogen, it is known that manufacturing hydrogen through traditional electrolysis methodologies can be inefficient for several reasons including, for example, the cost of energy required to operate the electolyzer, the mass over density causing elevated transportation costs when there is no pipeline, and the corresponding need for physical transportation of tanks or fuel cells.

The mobile transport can provide hydrogen power on a micro level without using power from the grid. Instead, it can use energy from a portable micro wind machine, for example. In addition, the mobility of the truck enables it to operate in a variety of conditions and proximate to a multitude of customers or other end users. For example, if located proximate to an affluent rich water source, such as a flood or sewage spill or a dump site, where it is possible to capture methane gas from the dump to fuel the electrolyzer, in addition to the micro wind option, or just from the captured methane gas alone, the mobile transport can be configured to collect the hydrogen in tanks or portable reusable hydrogen fuel cells to be distributed by locker or rack in a community or village for heat and electricity and communication services off grid. Such a capability can be valuable particularly for less developed regions that have no access to utilities or clean water.

Hydrogen provided by the mobile transports at this scale can changes the quality of life in villages and off-grid locales, such as demonstrated by the Coca Cola project, which manufactures and dispenses potable water. The mobile transports can therefore pop-up and provide a tank or fuel cell weekly, such as a pop-up in a local market or bazaar or directly to a dwelling of any kind. This hydrogen delivery can also replace dirtier and more expensive fuel sources like diesel and kerosene. In addition to powering homes, the hydrogen fuel cells provided by the mobile transports can also fuel machinery and farm equipment.

Figure 4:
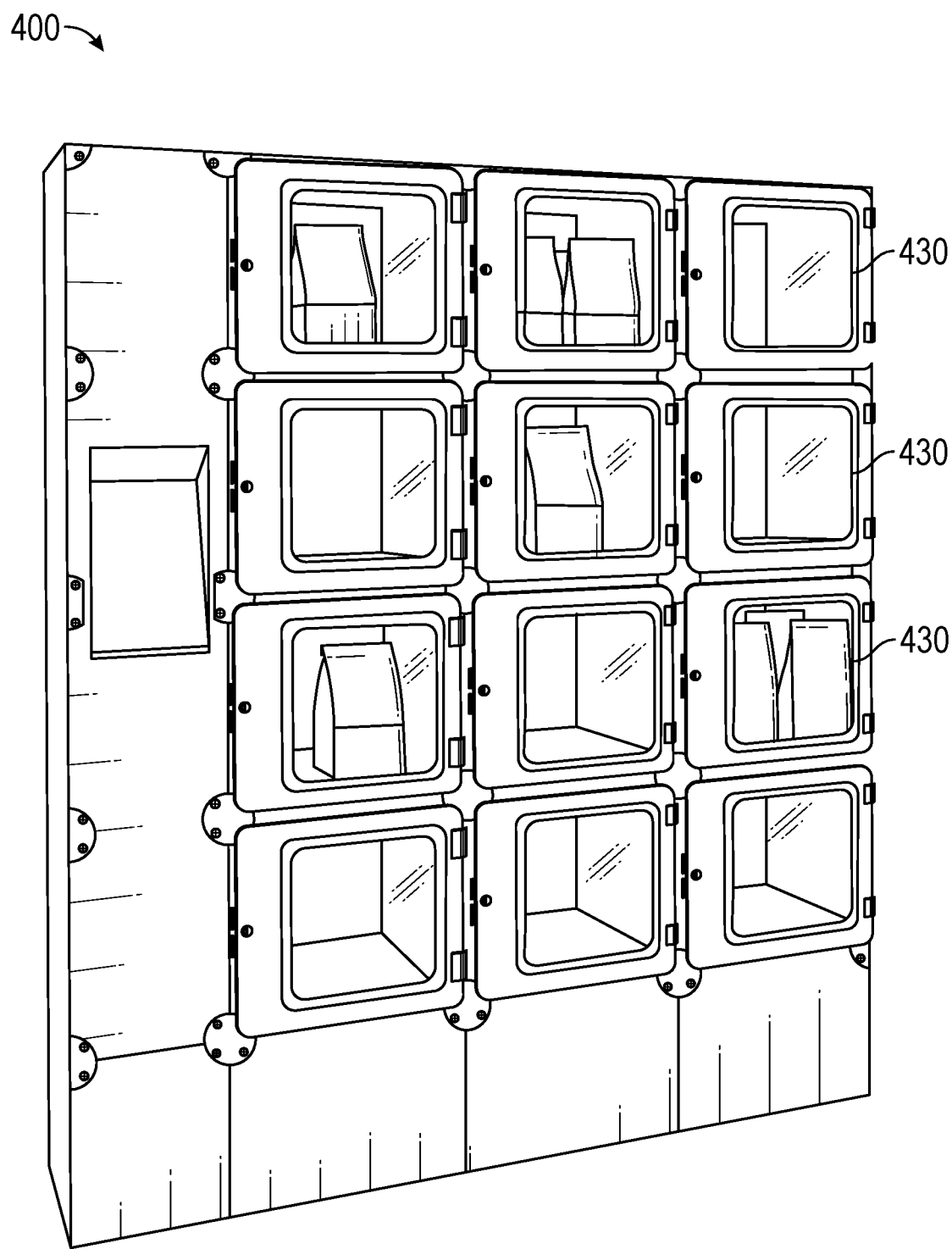
FIG. 4 shows an exemplary hub locker according to an embodiment.

In addition to mobile transports, the utility of the compartments for storage and pickup of items can be applied to other implementations. FIG. 4 provides an example of a hub locker 400 having a body 410, plurality of compartments 430 coupled to the body 410, and an operational control unit 450 coupled to the compartments. The body 410 includes a structure sufficient to hold and maintain the compartments 430 and operation control unit 450. The body 410 can be made of various materials, such as aluminum, steel, other metals, alloys, and/or fiberglass. The compartments 430 and operation control unit 450 can be configured and have the same structure and functionality as those present in the mobile transports 100, 200.

As a modification, the compartments 430 can also include a rear panel 432 that is configured to open and close in the same manner as the front panels 132, 232 of the mobile transports 100, 200. The hub locker 200 can be positioned or located so that only employees have access to a rear side of the hub locker 200 and thus only allow employees to have access to the rear panels 432 of the compartments 430. This design improves security and limits contacts to surfaces that might otherwise be contacted by both employees and users.

The delivery and order process of FIG. 3 applies similarly to the hub locker 400 with the exception of movement to the business and delivery addresses since the employees and users have to go to the hub locker 400 to put items in the compartments 430 and pick-up items from the compartments 430. But the making of the order, the access of the compartments, and the use of the germicidal and temperature controllers can be performed in the same way for the hub locker 400 as explained in relation to mobile transports 100 and 200.

Figure 5:
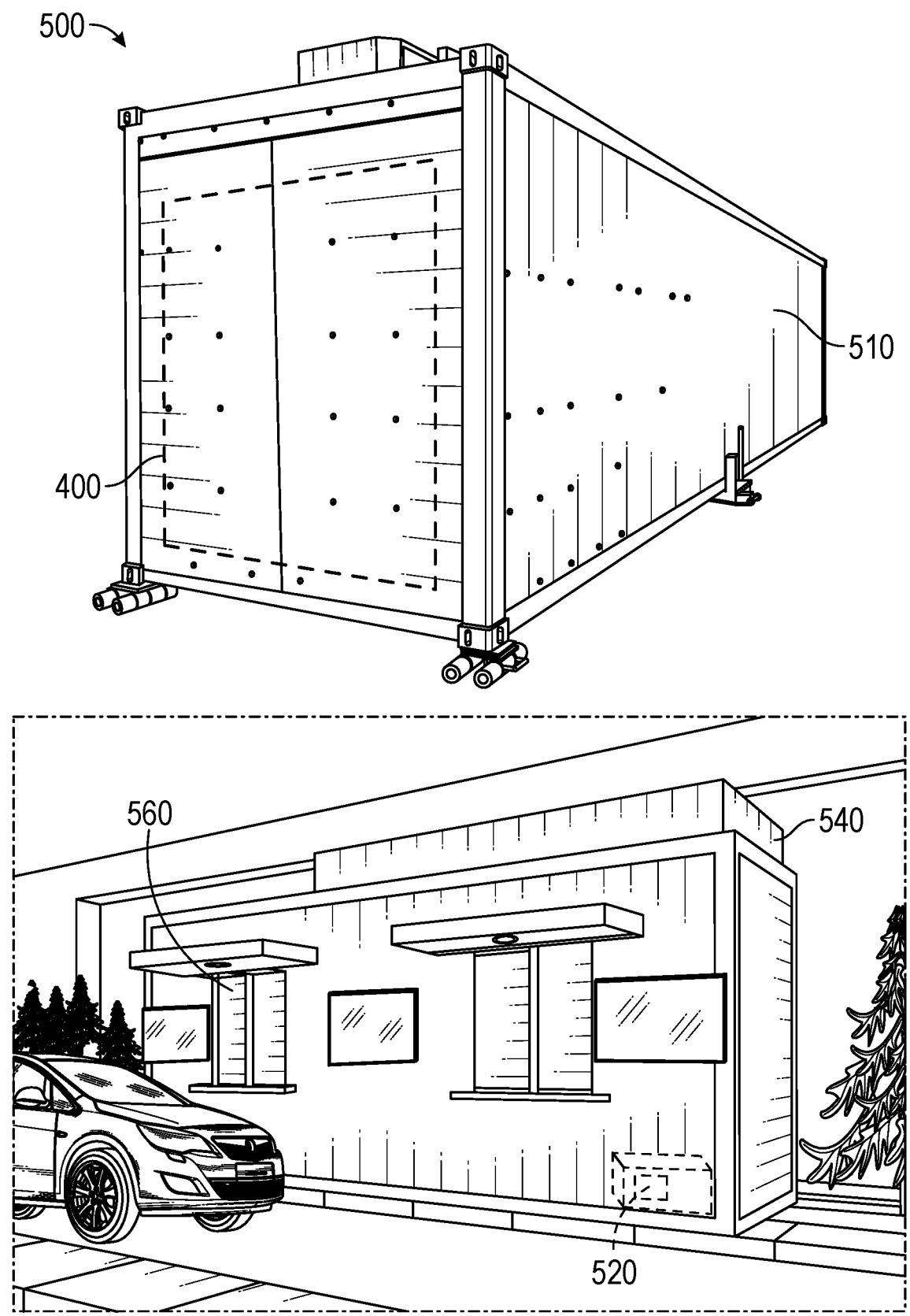
FIG. 5 shows an exemplary kitchen pod according to an embodiment.

Although the hub locker 400 can be implemented as a standalone implementation and placed in any of a variety of locations including, for example, malls, shopping centers, and parking lots, the hub locker 400 can be integrated with other components to provide a complete business pod, such as a kitchen pod. FIG. 5 provides an example of a kitchen pod according to an embodiment. As shown in FIG. 5, a kitchen pod includes an outer body 510, an integrated hub locker 400, a plurality of appliances 520, and a roof top patio 540. The kitchen pod 500 can also optionally include a drive through window 560.

The outer body 510 can be made of various materials, such as aluminum, steel, other metals, alloys, and/or fiberglass. The outer body 510 can be shaped to enclose all of the other components of the kitchen pod 500 including the hub locker 400 and the plurality of appliances 520 integrated to it. As a result, the outer body 510 provide an overall integrated structured for the kitchen pod 500 that enables the kitchen pod to be transportable to different locations such as malls, shopping centers, or parking lots. The outer body 510 can also include doors or shutters 512 that close off the interior of the kitchen hub to the outside. A top surface of the outer body 510 includes a roof top patio to which customers can access and use to enjoy meals prepared by the kitchen pod 500.

The appliances 520 can include any appliances as may be needed to make and store foodstuffs. For example, the appliances can include an oven 522, a stove 524, a microwave, 526, a sink 528, a refrigerator 530, and a grill 532. Which ones are included, how many of them, and where they are positioned can be adjustable according to the needs and preferences of the business purchasing and using the kitchen pod 500. The hub locker 400 in the kitchen pod 500 provides the same benefits as the compartments of the mobile transports by providing increased safety and convenience. For example, the germicidal and temperature controllers sanitize the compartments of the hub locker 400, minimize or eliminate the risk of the transmission of disease, minimize people-to-people interactions, and maintain the prepared foods at appropriate temperatures.

Moreover, the delivery and order process of FIG. 3 applies similarly to the kitchen pod 500 with the exception of movement to the business and delivery addresses since the employees and users go to the hub locker to put prepared foods in the compartments and pick-up items from the compartments. But the making of the order, the access of the compartments, and the use of the germicidal and temperature controllers can be performed in the same way for the hub locker.

Figure 6:
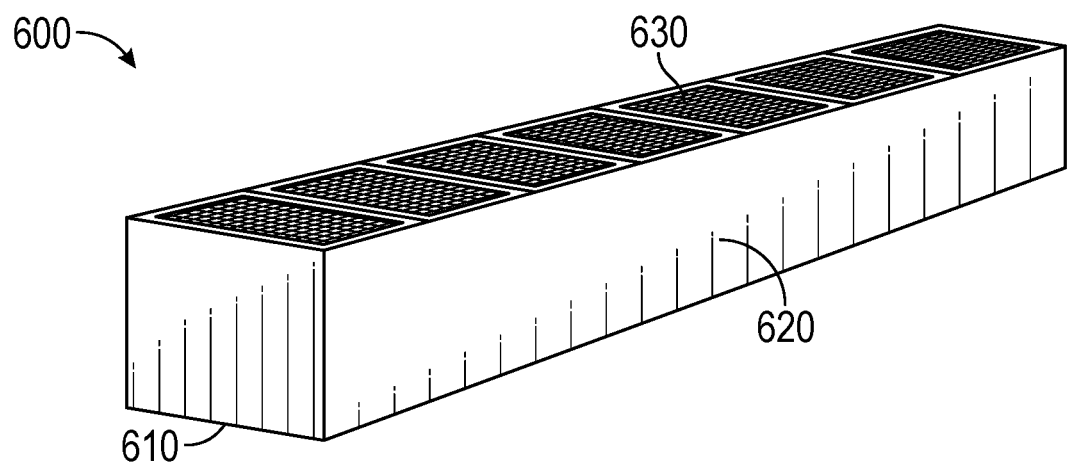
FIG. 6 shows an exemplary power storage and delivery device according to an embodiment.

FIG. 6 provides a power storage and delivery device according to an embodiment. As shown in FIG. 6. The power storage device 600 includes a body 610, battery storage 620, and solar panels 630. Each end of the body 610 can be used to mount additional solar panels 630 or to include information or logos, such as the logo of a company. Battery storage 620 can stored one or more batteries therein. Solar panels 630 can be used to generate energy that is stored in the batteries in battery storage 620. The solar panels 630 can be flat or tilted and have a robotic lever to tilt them up or down to maximize power generation. Although not shown, a micro wind turbine, a hydrogen electrolyzer, or other alternative energy source, can also be included to generate energy for storage in the batteries. The power storage device 600 can also be connected to the grid to charge the batteries, such as with high current CCS fast charging. The power storage device 600 can be configured with one or more plugs to enable the batteries to be charged from an external source and to provide power from the batteries to an external device.

The power storage device 600 can be mounted on, for example, mobile transport 100 by replacing some or all of the compartments 130 or mounted on some other form of mobile transportation. With this mobility, power storage device 600 can be delivered to locations that need power but have no access to the power grid. The power storage device 600 also provides a clean and rechargeable energy source instead of diesel or kerosene-based power conventionally used as a power source when access to the power grid is unavailable. With multiple power storage devices 600 and mounted for mobility, a system can be arranged to have a backup power storage device be alerted when batteries of an active power storage device are nearly exhausted and arrive at the location of the location of the active power storage device to replace it. In this manner, it is possible to maintain a continuous supply of uninterrupted power.

Various embodiments of the invention are contemplated in addition to those disclosed hereinabove. The above-described embodiments should be considered as examples of the present invention, rather than as limiting the scope of the invention. In addition to the foregoing embodiments of the invention, review of the detailed description and accompanying drawings will show that there are other embodiments of the present invention. Accordingly, many combinations, permutations, variations and modifications of the foregoing embodiments of the present invention not set forth explicitly herein will nevertheless fall within the scope of the present invention.

The invention claimed is:

1. A mobile transport for delivering temperature-controlled contents, comprising:
   a plurality of wheels;
   a vehicle body coupled to the wheels;
   a transmission coupled to the wheels and configured to drive the wheels;
   a power source coupled to the transmission and configured to power the transmission;
   a plurality of compartments coupled to the vehicle body, each of the plurality of compartments including an interior space and a front panel defining a wall of the interior space, wherein each front panel is operable to open and reveal the interior space of its compartment in response to a predetermined condition, and wherein each front panel includes a display screen on an external surface of each front panel;
   a temperature controller configured to individually control a temperature setting within at least one of the plurality of compartments, the temperature setting being below, at, or above an ambient temperature;
   a germicidal controller configured to provide a germicide to the interior space of each of the plurality of compartments;
   circuitry coupled to the power source; and
   a memory coupled to the circuitry comprising a plurality of instructions that, when executed by the circuitry, cause the mobile transport to:
   receive an order signal to pick up an item from a source, the order signal including the pickup location information, customer identification information, and delivery location information;
   open up a front panel of a first compartment after arriving at the pickup location in response to a message received by the circuitry;
   close the front panel of the first compartment after the item has been placed in the interior space of the first compartment;
   control the temperature controller to set the temperature setting for the first compartment according to a type of the item;
   after arriving at the delivery location, open the front panel of the first compartment in response to receiving an open request signal satisfying the predetermined condition, the open request signal including information relating to the customer identification information; and
   close the front panel of the first compartment after the item has been removed from the interior space of the first compartment,
   wherein the memory further comprises an instruction executed by the circuitry to cause the mobile transport to display a first image on the front panel of the first compartment indicative of the item in the first compartment and to display a second image, different from the first image, on a front panel of a second compartment, different from the first compartment, wherein the second image is indicative of an item stored in the second compartment.

2. The mobile transport of claim 1, the memory further comprising an instruction executed by the circuitry to cause the mobile transport to control the germicidal controller to provide the germicide to the interior space of the first compartment after the front panel of the first compartment is closed.

3. The mobile transport of claim 1, wherein the open request signal includes a unique identifier received from a mobile device, and the predetermined condition is satisfied when the received unique identifier matches information included in the customer identification information.

4. The mobile transport of claim 3, wherein the unique identifier is one of a transaction identifier or a QR code.

5. The mobile transport of claim 1, the memory further comprising an instruction executed by the circuitry to cause the mobile transport to control the germicidal controller to provide the germicide to the interior space of the first compartment after receiving the order signal and prior to opening the front panel of the first compartment at the pickup location.

6. The mobile transport of claim 5, the memory further comprising an instruction executed by the circuitry to cause the mobile transport to control the germicidal controller to provide the germicide to the interior space of the first compartment after closing the front panel of the first compartment with the item inside the first compartment and prior to arriving at the delivery location.

7. The mobile transport of claim 1, the memory further comprising instructions executed by the circuitry to cause the mobile transport to:
determine a type of the item placed in the interior space of the first compartment; and
control the temperature controller to set the temperature setting for the first compartment according to the determined type of the item.

8. The mobile transport of claim 1, wherein the germicidal controller includes one or more UV light sources, the memory further comprising an instruction executed by the circuitry to cause the mobile transport to control the germicidal controller to activate the one or more UV light sources after the front panel of the first compartment is closed.

9. The mobile transport of claim 1, wherein the germicidal controller includes a germicidal spray source, the memory further comprising an instruction executed by the circuitry to cause the mobile transport to control the germicidal controller to spray germicide from the germicidal spray source after the front panel of the first compartment is closed.

10. The mobile transport of claim 1, wherein the circuitry includes a GPS circuit configured to receive location information for the mobile transport, the memory further comprising instructions executed by the circuitry to cause the mobile transport to:
access the location information received by the GPS circuit;
determine a route between a current location of the mobile transport based on the location information and the pickup location information; and
control the mobile transport to move from the current location to the pickup location according to the determined route.

11. The mobile transport of claim 1, wherein the power source includes at least one of a solar panel, a wind turbine, a hydrogen fuel cell, or a hydrogen electrolyzer,
wherein the mobile transport further includes at least one battery for storing power generated by the power source, and
wherein the mobile transport further includes a power outlet for providing power from the at least one battery.

12. The mobile transport of claim 1, further comprising a plurality of lighting elements, wherein each lighting element is located on an external surface of the mobile transport, wherein each lighting element is positioned around a corresponding one of the plurality of compartments, and wherein the memory further comprises an instruction executed by the circuitry to cause the lighting element positioned around the first compartment to be activated after arriving at the delivery location.

13. A method for delivering temperature-controlled contents in a mobile transport, comprising a plurality of wheels, a vehicle body coupled to the wheels, a transmission coupled to the wheels and configured to drive the wheels, a power source coupled to the transmission and configured to power the transmission, a plurality of compartments coupled to the vehicle body, each of the plurality of compartments including an interior space and a front panel defining a wall of the interior space, wherein each front panel is operable to open and reveal the interior space of its compartment in response to a predetermined condition and includes a display screen on an external surface of each front panel, a temperature controller configured to individually control a temperature setting within at least one of the plurality of compartments, the temperature setting being below, at, or above an ambient temperature, and a germicidal controller configured to provide a germicide to the interior space of each of the plurality of compartments, the method comprising:
receiving an order signal to pick up an item from a source, the order signal including the pickup location information, customer identification information, and delivery location information;
after the mobile transport arrives at the pickup location, opening a front panel of a first compartment in response to a received message;
closing the front panel of the first compartment after the item has been placed in the interior space of the first compartment;
controlling the temperature controller to set the temperature setting for the first compartment according to a type of the item;
after the mobile transport arrives at the delivery location, opening the front panel of the first compartment in response to receiving an open request signal satisfying the predetermined condition, the open request signal including information relating to the customer identification information; and
closing the front panel of the first compartment after the item has been removed from the interior space of the first compartment,
wherein the method further comprises displaying a first image on the front panel of the first compartment indicative of the item in the first compartment and displaying a second image, different from the first image, on a front panel of a second compartment, different from the first compartment, wherein the second image is indicative of an item stored in the second compartment.

14. The method of claim 13, the method further comprising controlling the germicidal controller to provide the germicide to the interior space of the first compartment after the front panel of the first compartment is closed.

15. The method of claim 13, wherein the open request signal includes a unique identifier received from a mobile device, and the predetermined condition is satisfied when the received unique identifier matches information included in the customer identification information.

16. The method of claim 15, wherein the unique identifier is one of a transaction identifier or a QR code.

17. The method of claim 13, the method further comprising causing the mobile transport to control the germicidal controller to provide the germicide to the interior space of the first compartment after receiving the order signal and prior to opening the front panel of the first compartment at the pickup location.

18. The method of claim 17, the method further comprising causing the mobile transport to control the germicidal controller to provide the germicide to the interior space of the first compartment after closing the front panel of the first compartment with the item inside the first compartment and prior to arriving at the delivery location.

19. The method of claim 13, the method further comprising:
   determining a type of the item placed in the interior space of the first compartment; and
   controlling the temperature controller to set the temperature setting for the first compartment according to the determined type of the item.

20. The method of claim 13, wherein the germicidal controller includes one or more UV light sources, the method further comprising controlling the germicidal controller to activate the one or more UV light sources after the front panel of the first compartment is closed.

21. The method of claim 13, further comprising
   receiving power from at least one of a solar panel, a wind turbine, a hydrogen fuel cell, or a hydrogen electrolyzer;
   storing the received power in at least one battery; and
   providing power from the at least one battery.

22. The method of claim 13, wherein the mobile transport further includes a plurality of lighting elements, each lighting element being located on an external surface of the mobile transport and positioned around a corresponding one of the plurality of compartments, the method further comprising activating the lighting element positioned around the first compartment after arriving at the delivery location.

* * * * *